United States Patent [19]
Salama

[11] Patent Number: 5,893,826
[45] Date of Patent: Apr. 13, 1999

[54] ARTIFICIAL SPHINCTER URINARY CONTROL SYSTEM

[76] Inventor: Fouad A. Salama, 3220 Valley Ridge Ct., West Des Moines, Iowa 50265

[21] Appl. No.: 08/907,830

[22] Filed: Aug. 14, 1997

[51] Int. Cl.[6] .................................................. A61F 2/02
[52] U.S. Cl. ........................ 600/31; 600/29; 128/DIG. 25
[58] Field of Search ......................... 600/29–31; 251/5; 128/DIG. 25

[56] References Cited

U.S. PATENT DOCUMENTS

| | | |
|---|---|---|
| 2,455,859 | 12/1948 | Foley . |
| 2,533,924 | 12/1950 | Foley . |
| 3,538,917 | 11/1970 | Selker . |
| 3,642,005 | 2/1972 | McGinnis . |
| 3,720,200 | 3/1973 | Laird . |
| 3,731,670 | 5/1973 | Loe . |
| 3,744,063 | 7/1973 | McWhorter et al. . |
| 3,750,194 | 8/1973 | Summers . |
| 3,758,073 | 9/1973 | Schulte . |
| 3,853,122 | 12/1974 | Strauch et al. . |
| 3,854,469 | 12/1974 | Giori et al. . |
| 3,863,622 | 2/1975 | Buuck . |
| 4,222,377 | 9/1980 | Burton . |
| 4,386,601 | 6/1983 | Trick . |
| 4,428,365 | 1/1984 | Hakky . |
| 4,549,531 | 10/1985 | Trick . |
| 4,552,128 | 11/1985 | Haber . |
| 4,587,954 | 5/1986 | Haber . |
| 4,587,955 | 5/1986 | Gengler . |
| 4,679,546 | 7/1987 | Van Waalwijk Van Doorn et al. . |
| 4,878,889 | 11/1989 | Polyak . |
| 4,968,294 | 11/1990 | Salama . |
| 5,004,454 | 4/1991 | Beyar et al. ............................... 600/30 |
| 5,012,822 | 5/1991 | Schwarz . |
| 5,306,226 | 4/1994 | Salama . |
| 5,782,916 | 7/1998 | Pintauro et al. ........................... 623/12 |

*Primary Examiner*—Michael Peffley
*Assistant Examiner*—Roy Gibson
*Attorney, Agent, or Firm*—Zarley, McKee, Thomte, Voorhees & Sease

[57] ABSTRACT

An inflatable cuff used as an artificial sphincter may be used in either of two different ways. The first embodiment involves the cuff encircling the urethra for maintaining pressure on it to occlude it except when voiding the bladder. The second embodiment involves placing a one-way valve in the urethra which is encircled by the inflatable cuff such that the cuff is only inflated when it is desired to void the bladder by opening the valve in the urethra through pressure being applied to the exterior of the valve body. In each embodiment a syringe-type pump bulb is used which is connected to a one-way valve in turn connected to a tube to the inflatable cuff. The bulb side wall has sufficient memory to cause it to return to its normal expanded condition which causes the suction of fluid from the cuff when the manually operated valve is actuated. Fluid pumped to the cuff through the valve causes a positive pressure on the cuff side of the valve blade elements and a negative pressure on the bulb side which combine to assist in maintaining the valve in a sealed closed condition.

18 Claims, 4 Drawing Sheets

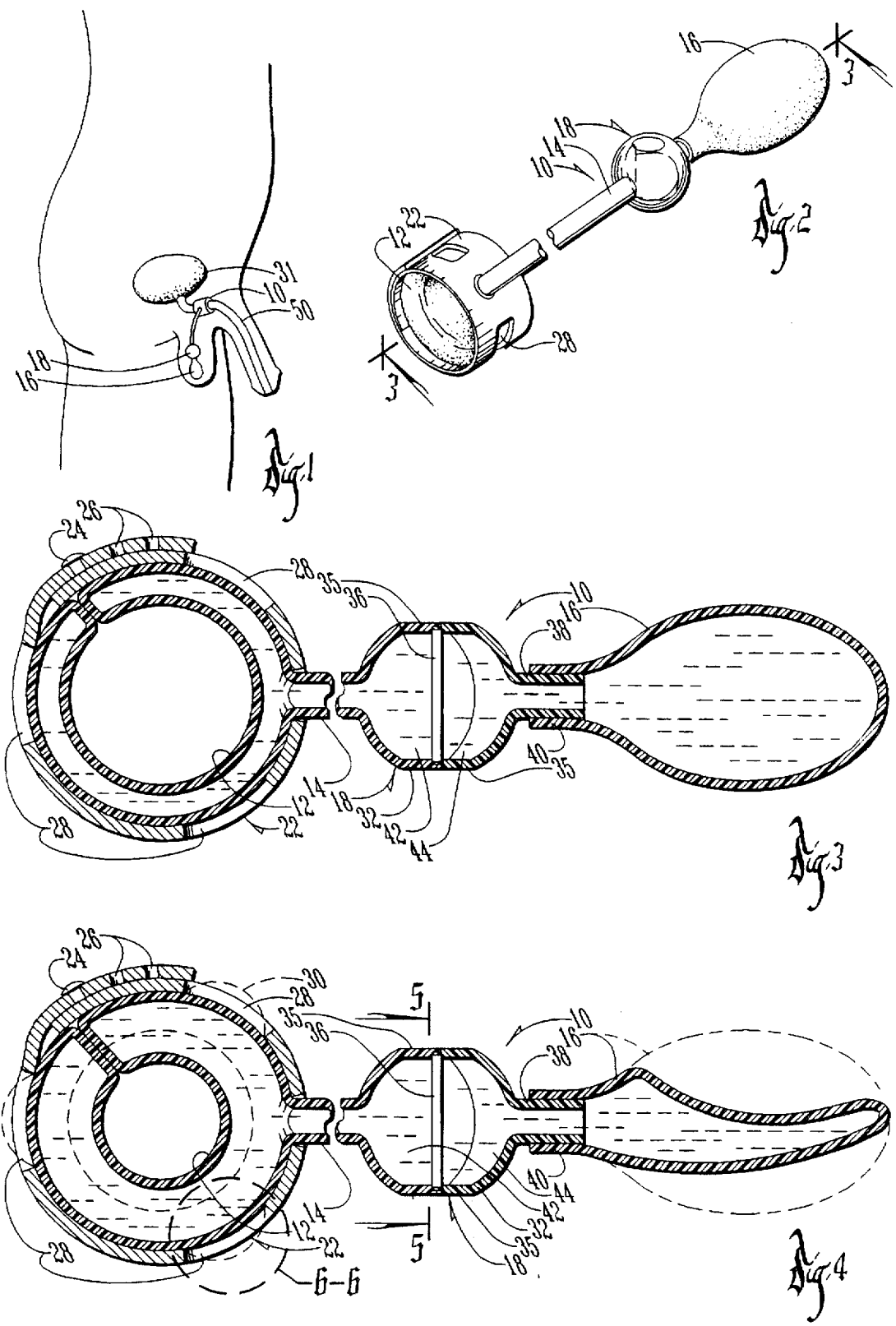

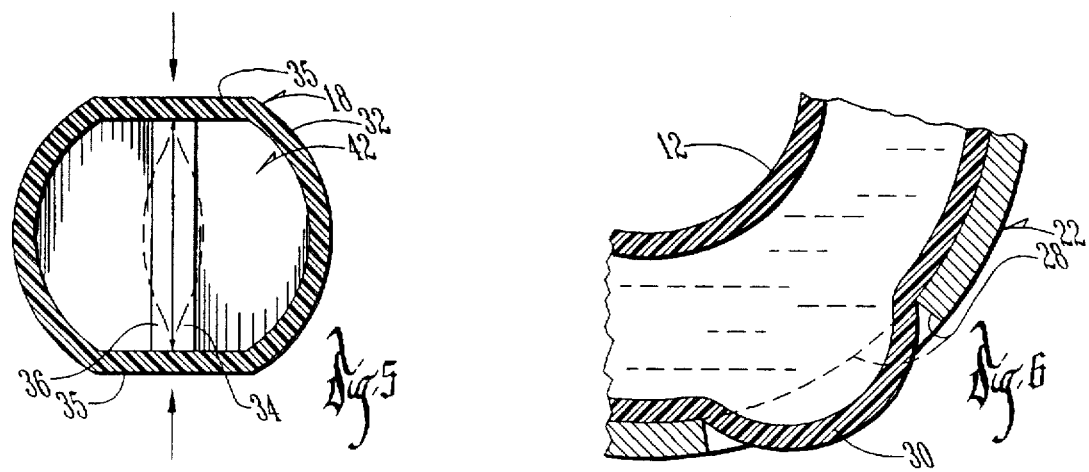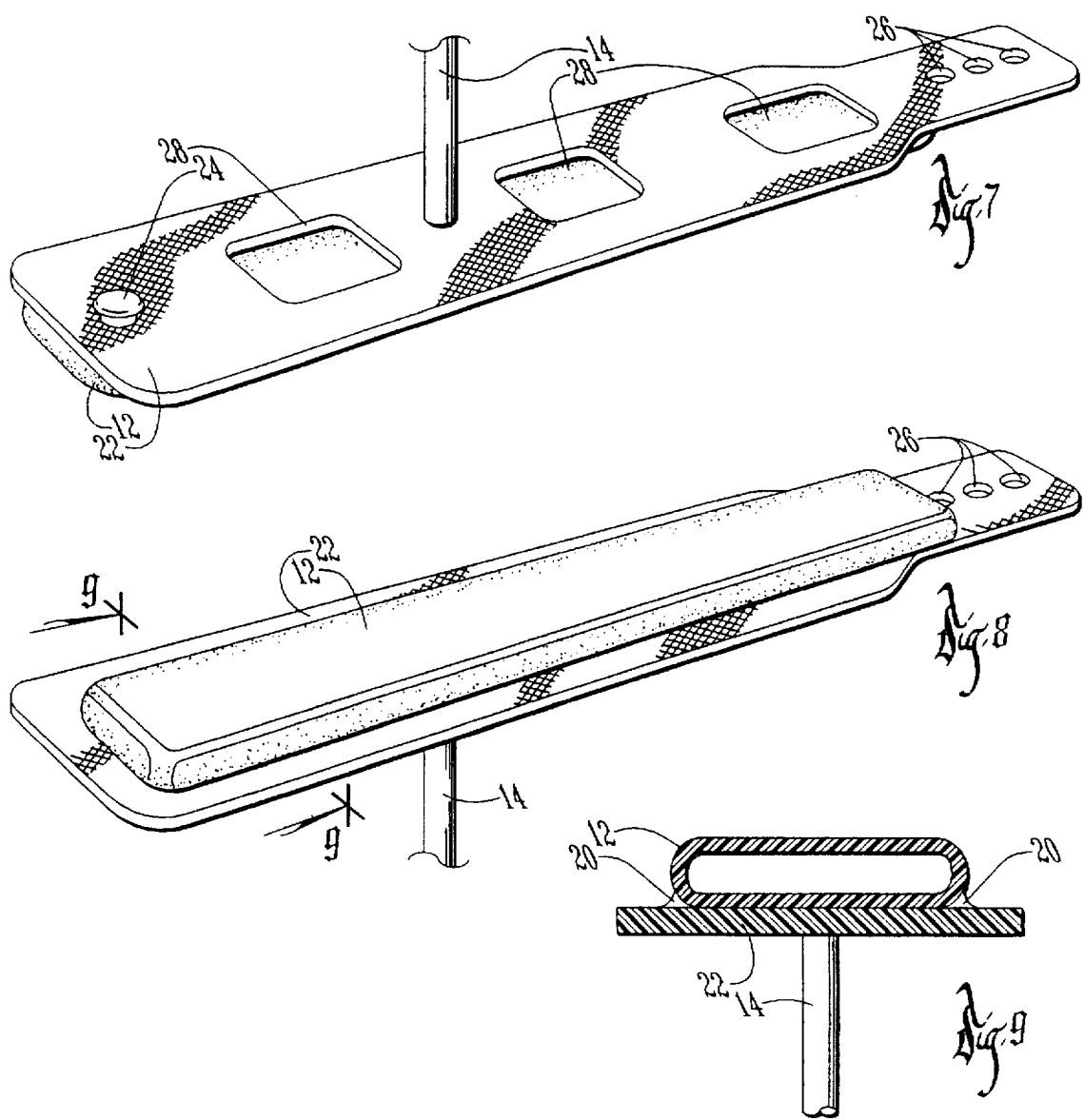

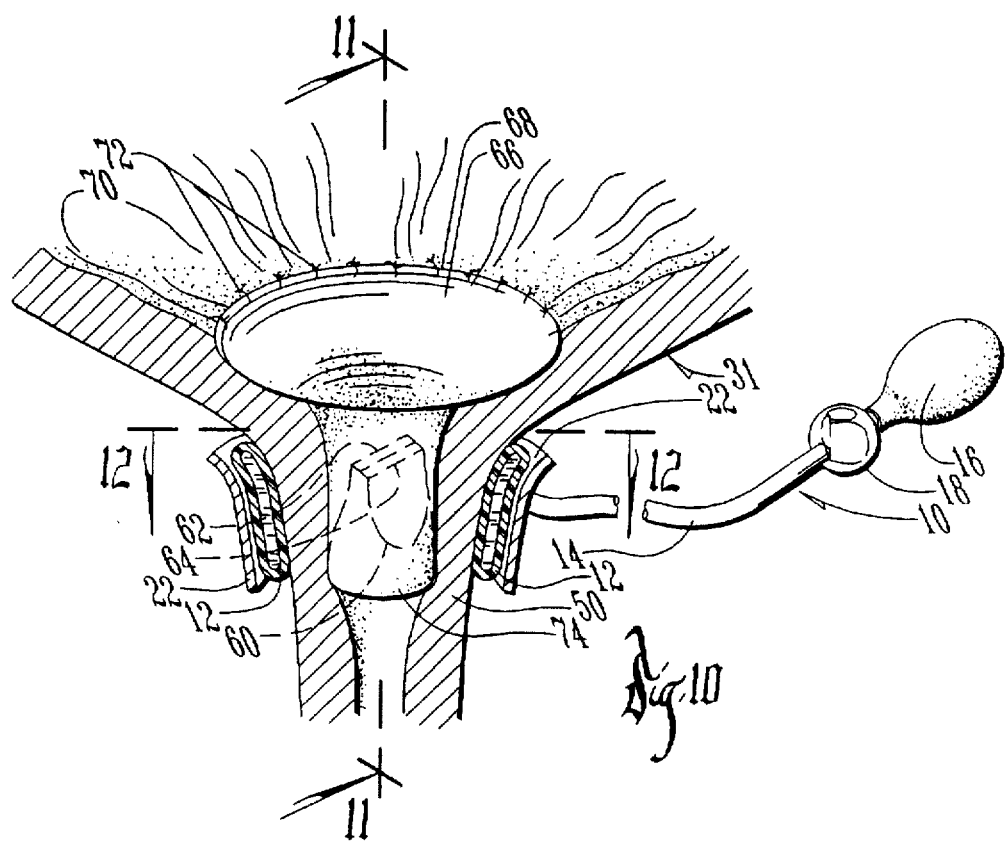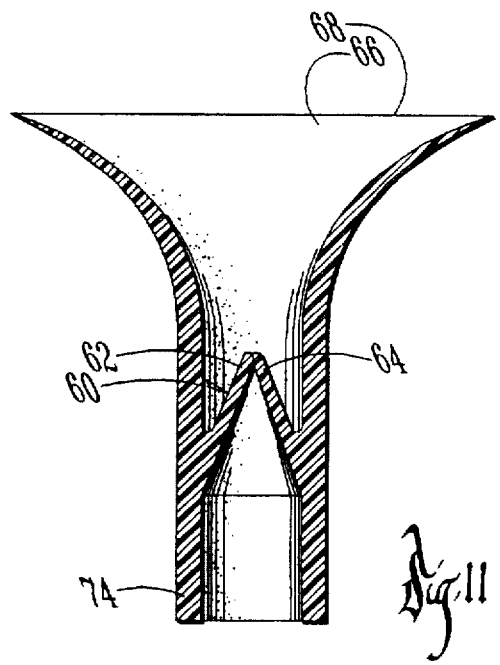

ARTIFICIAL SPHINCTER URINARY CONTROL SYSTEM

BACKGROUND OF THE INVENTION

An artificial sphincter is commercially available from American Medical Systems, Inc. (AMS), Gordon Valley, Minn., and is disclosed in U.S. Pat. No. 4,222,377 issued Sep. 16, 1980.

The present invention is an improvement upon the AMS system which includes an inflatable cuff encircling the urethra with the cuff being maintained in an inflated condition by a pump whereby the urethra is intended to be occluded to urine flow from the bladder. If a person desires to void the bladder, a valve is manually operated which allows fluid pressure in the cuff to be relieved and fluid flows through the valve into the pump. Deflation of the cuff is totally dependent upon pressure within the cuff forcing the fluid out of the cuff and back to the pump. This is a slow process and there is need for a more instantaneous way to prepare the cuff for voiding the bladder. The first embodiment of the present invention provides an answer to this problem.

A second problem experienced with the AMS system is that the cuff maintains continuous pressure on the urethra in order to prevent undesired urine flow from the bladder. It is difficult to achieve the optimum pressure level considering the advantages and disadvantages of too much or too little pressure. The amount of pressure that will assure that there is no leakage will cause damage to the urethra by cutting off blood flow and too little pressure will result in bladder leakage. The second embodiment of the present invention provides an answer to this problem.

SUMMARY OF THE INVENTION

The first embodiment of this invention utilizes a syringe-type bulb which functions as a two-way pump. The bulb has a side wall with memory. The side wall normally takes on a generally spherical shape and when manually compressed wants to return to its normally expanded condition. The bulb is compressed to pump fluid through a one-way valve to the inflatable cuff. The cuff and the one-way valve taken with the bulb comprise a closed system containing substantial fluid. The bulb when manually compressed remains in its deformed condition until the one-way valve is manually opened whereupon the bulb in returning to its expanded normal condition returns fluid from the cuff to the bulb. When the bulb is compressed, it creates negative pressure within the bulb which functions to suck the fluid from the cuff for return to the bulb through the open valve. The strength and memory of the bulb side wall will determine the instantaneous speed of the fluid return to the bulb when the one-way valve is actuated.

The one-way valve includes blade elements converging toward the cuff and thus are normally maintained in a closed sealing condition by positive pressure between the cuff and the forward side of the blade elements while negative pressure created by the compressed bulb memory impacts upon rear side of the blades tending to further draw them into sealing engagement with each other.

The second embodiment, while preferably utilizing the two-way syringe-type bulb pump of the first embodiment and one-way valve with the inflatable cuff, does not use the inflatable cuff to normally constrict the urethra but instead uses the inflatable cuff to open a normally closed one-way valve in the urethra. This arrangement totally eliminates any damaging continuous pressure being applied to the urethra. The only pressure that is applied to the urethra is momentarily when it is desired to void the bladder.

The one-way valve in the proximal urethra is an integral part of a funnel-type seal that is placed in the neck and orifice of the bladder at proximal urethra to prevent leakage around the outside of the valve in the urethra. The funnel shape of the seal provides a peripheral flange which matingly engages the side wall of the bladder and orifice. Urine from the bladder is permitted to flow naturally into the inlet end of the funnel-shaped seal and is blocked by the one-way valve until the valve is actuated to an open position through inflation of the cuff encircling it. The funnel-shaped seal is implanted in the bladder neck, orifice and proximal urethra through use of conventional sutures or the like.

BRIEF DESCRIPTION OF THE DRAWINGS

FIG. 1 is a fragmentary frontal view of a body illustrating the urethra in association with the artificial sphincter of this invention.

FIG. 2 is a fragmentary perspective view of the first embodiment of the artificial sphincter of this invention.

FIG. 3 is a cross-sectional view taken along line 3—3 in FIG. 2 showing the inflatable cuff deflated, the valve normally closed and the bulb-type pump normally expanded.

FIG. 4 is a view similar to FIG. 3 but showing the cuff inflated and the bulb pump contracted.

FIG. 5 is a cross-sectional view taken along line 5—5 in FIG. 4 showing the converging blade elements of the one-way valve in a normally closed condition.

FIG. 6. is a fragmentary cross-sectional view taken along line 6—6 in FIG. 4 showing the pressure relief means including an opening in the frame encircling the inflatable cuff balloon, with the frame having an opening through which the balloon may expand to relieve the pressure around the urethra.

FIG. 7 is a fragmentary perspective view of the combined cuff and frame.

FIG. 8 is a view similar to FIG. 7 but showing the opposite side thereof.

FIG. 9 is a cross-sectional view taken along line 9—9 in FIG. 8.

FIG. 10 is a fragmentary perspective view of the second embodiment of the artificial sphincter of this invention.

FIG. 11 is a cross-sectional view taken along line 11—11 in FIG. 10.

DETAILED DESCRIPTION OF THE INVENTION

Figure 12:
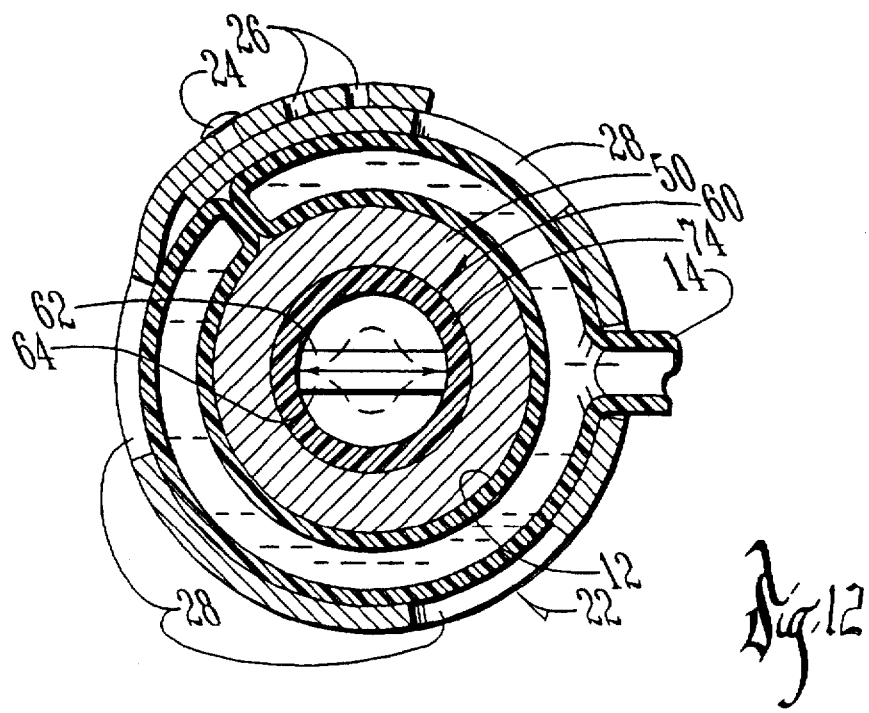
FIG. 12 is a cross-sectional view taken along line 12—12 in FIG. 10.

The first embodiment of this invention is disclosed in FIGS. 1-9 and is referred to generally in FIG. 2 by the Reference 10. The artificial sphincter 10 of FIG. 2 is seen to include an inflatable balloon cuff 12 which receives fluid through a tube 14 from a syringe-type bulb pump 16 connected to a one-way valve 18.

The cuff 12 is secured by adhesive 20 as seen in FIG. 9 to a flat frame 22 which includes a button 24 to be received in one of a plurality of openings 26 when the cuff is formed into a circle as seen in FIGS. 2-4.

A trio of pressure-relief openings 28 are formed in the frame 22 through which the cuff 12 expands as seen by the cuff portion 30 in FIG. 6 which has expanded through opening 28. This sudden expansion can be due to any number of different reasons including gas pressure in the stomach causing pressure on the bladder, coughing or physical activity causing pressure on the bladder 31. It is desired to maintain a constant pressure in the cuff as it is applied to the urethra to avoid discomfort and possible tissue damage.

The valve 18 includes a valve body 32 and a pair of blade elements 34 and 36 which converge towards the cuff 12. A pair of oppositely disposed flattened surfaces 35 are provided on opposite sides of the valve body 32 for positioning the fingers to operate valve 18 for moving the blade elements 34 and 36 to an open position. The valve body 32 includes an outlet tube portion 38 which is received in the open end portion 40 of the pump/syringe-type bulb 16. The bulb 16 includes a side wall made of an appropriate rubber or plastic material that has sufficient memory to cause it to normally assume an expanded appearance as seen in FIGS. 2 and 3. In FIG. 4, the bulb 16 is shown contracted as a result of it having been squeezed to pump fluid from the bulb through the valve 18 into the cuff 12. This pumping operation creates a positive pressure in the valve body 18 on the cuff side in chamber portion 42 and a negative pressure in the rear chamber portion 44. Both of these pressure conditions tend to assist in maintaining the valve blade elements 34 and 36 in a closed sealed condition. When it .s desired to void the bladder, manual pressure is applied to the flattened areas 35 on the valve body 32 which causes the blade elements 34 and 36 to spread apart. This valve operation will instantaneously cause fluid to be sucked from the cuff 12 by the bulb 16 returning to its expanded condition in response to memory of the bulb side wall.

It is understood that as seen in FIG. 1 the entire artificial sphincter 10 is implanted into the male or female body with the cuff 12 encircling the urethra 50. The preferred material from which the cuff 12 is made is a reinforced silicone material from Specialty Silicone Fabricators, Inc., Paso Robles, Calif. The bulb 16 and valve 18 can be conveniently implanted in the labia of a female or the scrotum of a male. Depending on the size of the bulb 16, the pressure in the balloon cuff 12 may vary between 0.71 PSI and 1.13 PSI.

The second embodiment of this invention is disclosed in FIGS. 10–13. As discussed, the artificial sphincter 10 in the first embodiment was used to normally apply a continuous pressure to the urethra to occlude it except when voiding. The artificial sphincter 10 of the second embodiment is used to open a normally closed valve 60 positioned in the proximal end of the urethra as seen in FIG. 10.

The valve 60 includes a pair of blades 62 and 64 which converge toward the bladder 31. The valve 60 is an integral part of a funnel-shaped retainer seal 66. The retainer includes an outwardly flaring flange 68 which matingly engages the inside surface 70 of the bladder neck and orifice to form a seal therebetween. The funnel retainer seal may be held in place in any conventional manner, including sutures 72. The funnel 66 includes a throat portion 74 which extends into the proximal end of the urethra 50.

Figure 13:
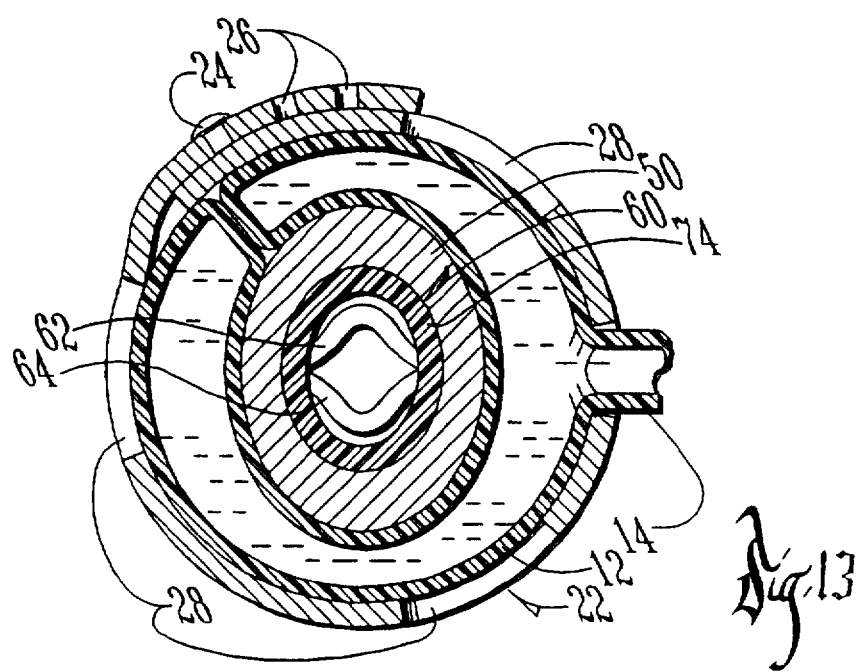
FIG. 13 a cross-sectional view similar to FIG. 12 but showing the cuff inflated thereby actuating the valve in the urethra to an open condition.

Thus, in operation it is seen that the one-way valve 60 is normally closed to urine flow through the funnel retainer seal 66 positioned in the urethra 50. The flange 68 of the funnel 66 prevents leakage between the side wall 70 of the bladder neck and orifice and the funnel. When it is desired to void the bladder, it is only necessary to operate the pump bulb 16 to inflate the balloon cuff 12 which applies pressure to the valve 60 to cause it to open as seen in FIG. 13, thus allowing urine flow therethrough. Operation of the one-way valve 18 connected to the pump bulb 16 will cause immediate deflation of the balloon cuff 12 thereby allowing the valve 60 to return to its normally closed condition. It is seen that pressure is only applied to the urethra 50 during the few moments required for voiding, as opposed to continuous pressure being applied except during the time of voiding as is the case with the first embodiment of FIGS. 1–9. A suitable silicone material may be used for fabrication of the funnel retainer seal 66. The pressure in the balloon cuff 12 to open the valve 60 is much less than the minimum pressure of 0.71 PSI required to close the urethra 50 in the first embodiment.

What is claimed is:

1. An artificial sphincter system adapted for reversibly occluding a passageway in a vessel, said system comprising, a normally closed first valve adapted to be positioned in said vessel, said valve being actuateable to an open condition in response to external pressure being applied to it, inflatable cuff means adapted for substantially encircling said vessel and said valve to be opened and closed for constricting said vessel and said valve in response to fluid pressure;

means for supplying fluid under pressure comprising a manually deformable, elastomeric bulb in fluid flow configuration with said cuff means, said bulb serving as both a fluid reservoir and a pump;

flow passage means connecting said bulb with the inside of said cuff means, a one-way valve means in said flow passage means for normally restricting flow from said cuff to said bulb, said one-way valve means being normally closed but actuateable to an open position in response to fluid pressure from said bulb, and said one-way valve means being actuateable to an open position in response to manual operation allowing fluid flow from said cuff to said bulb, said cuff, bulb and flow passageway comprising a closed system through which fluid is adapted to reversibly flow between said cuff and said bulb, and said bulb having a normal expanded condition due to memory of the bulb when said cuff is deflated and a contracted condition when said cuff is inflated whereby when said one way valve means is manually operated to said open position, said bulb memory returns said bulb to its normal expanded condition causing said bulb to function as a two-way pump for returning said fluid from said cuff to said bulb.

2. The artificial sphincter system of claim 1 wherein said inflatable cuff includes a frame encircling said cuff, said frame including relief opening means through which said cuff may expand in response to increased pressure on said cuff from said vessel to assist in maintaining a constant pressure around said vessel.

3. The artificial sphincter system of claim 2 wherein said frame includes opposite ends having fastening means for interconnecting said opposite ends.

4. The artificial sphincter system of claim 2 wherein said frame encircling said cuff restricts outward expansion of said cuff except through said relief opening means.

5. The artificial sphincter system of claim 1 wherein said one-way valve means includes a valve body having normally closed converging blade elements converging towards said cuff means being operable to allow fluid flow from said cuff means by application of external pressure on opposite sides of the valve body to open the blade elements, and said blade elements having front sides facing said cuff means and rear sides facing said bulb.

6. An artificial sphincter system adapted for reversibly occluding a passageway in a vessel, said system comprising,
- a normally closed valve adapted to be positioned in said vessel, said valve being actuateable to an open condition in response to external pressure being applied to it,
- inflatable cuff means adapted for substantially encircling said vessel and said valve, and
- a pump means in fluid communication with said cuff means to selectively inflate and deflate said cuff means whereby said valve is actuated to said open condition when said cuff is inflated thereby allowing fluid flow in said vessel through said valve.

7. The artificial sphincter system of claim 6 and a flow passageway connects said pump with said cuff means, a second valve is positioned in said flow passageway between said cuff means and said pump, said second valve being a normally closed one-way valve but actuateable to an open condition in response to fluid pressure from said pump.

8. The artificial sphincter system of claim 7 wherein said cuff means, said pump and flow passageway comprise a closed system in which fluid reversibly flows between said cuff and said pump, said pump is a bulb, said bulb having a normal expanded condition due to memory of the bulb when said cuff is deflated and a contracted condition when said cuff is inflated whereby when said second valve is actuated to said open position, said bulb memory returns said bulb to its normal expanded condition causing said bulb to function as a two-way pump for returning fluid from said cuff to said bulb.

9. The artificial sphincter system of claim 6 wherein said inflatable cuff includes a frame encircling said cuff, said frame including relief opening means through which said cuff may expand in response to sudden increased pressure on said cuff from said vessel to assist in maintaining a constant pressure around said vessel.

10. The artificial sphincter system of claim 9 wherein said frame includes opposite ends having fastening means for interconnecting said opposite ends.

11. The artificial sphincter system of claim 9 wherein said frame encircling said cuff restricts outward expansion of said cuff except through said relief opening means.

12. The artificial sphincter system of claim 6 wherein said second valve includes a valve body having normally closed converging blade elements converging towards said cuff means being operable to allow fluid flow from said cuff means by application of external pressure on opposite sides of the valve body to open the blade elements, and said blade elements having front sides facing said cuff means and rear sides facing said bulb.

13. The artificial sphincter system of claim 6 wherein said first valve is an integral part of a funnel-shaped seal adapted to be positioned in the bladder neck and orifice and proximal urethra, said funnel-shaped seal includes an inlet end having an outwardly flared peripheral flange adapted for matingly and sealingly engaging a neck and orifice side wall to prevent urine leaking between a urethra side wall and the funnel-shaped seal.

14. The artificial sphincter system of claim 13 wherein said funnel-shaped seal is adapted to be held in the neck and orifice of the bladder by fastening means connecting the seal to the neck and orifice of the bladder.

15. An artificial sphincter system adapted for reversibly occluding a passageway in a vessel, comprising
- a normally, closed valve adapted to be positioned in said vessel, said valve being actuateable to an open condition in response to an increase in pressure being applied to the valve through a urethral wall, and
- said valve being an integral part of a funnel shaped seal adapted to be positioned in the bladder neck and orifice and proximal urethra, said funnel shaped seal including an inlet end having an outwardly flared peripheral flange adapted for matingly and sealingly engaging a neck and orifice side wall to prevent urine leaking between said urethra side wall and the funnel-shaped seal.

16. An artificial sphincter system adapted for reversibly occluding a passageway in a vessel, said system comprising,
- a normally closed valve adapted to be positioned in said vessel, said valve being actuateable to an open condition in response to an increase in pressure being applied to the valve through a urethral wall,
- expandable pressure means adjacent said valve adapted to be positioned externally of said passageway for opening said valve.

17. The artificial sphincter of claim 16 and a control means remote to said pressure means for operating said pressure means.

18. The artificial sphincter of claim 16 wherein the expandable pressure means is an inflatable means.

* * * * *